(12) United States Patent
Melching

(10) Patent No.: US 7,214,022 B2
(45) Date of Patent: May 8, 2007

(54) OBJECT STORAGE DEVICE AND CLIMATE-CONTROLLED CABINET

(75) Inventor: Achim Melching, Langenselbold (DE)

(73) Assignee: Thermo Fisher Scientific Inc., Langenselbold (DE)

( * ) Notice: Subject to any disclaimer, the term of this patent is extended or adjusted under 35 U.S.C. 154(b) by 310 days.

(21) Appl. No.: 10/349,953

(22) Filed: Jan. 24, 2003

(65) Prior Publication Data

US 2004/0004415 A1 Jan. 8, 2004

(30) Foreign Application Priority Data

Jan. 27, 2002 (DE) ............... 102 02 873

(51) Int. Cl.
*G05G 11/00* (2006.01)
(52) U.S. Cl. .................... 414/277; 414/561
(58) Field of Classification Search ........ 414/277, 414/591, 266, 561; 901/16, 26
See application file for complete search history.

(56) References Cited

U.S. PATENT DOCUMENTS

| | | | | |
|---|---|---|---|---|
| 2,765,928 A | * | 10/1956 | Riemenschneider | 212/319 |
| 3,268,097 A | | 8/1966 | Armington, Jr. et al. | 214/16.4 |
| 5,183,999 A | * | 2/1993 | Hakenewerth et al. | 235/379 |
| 5,291,001 A | * | 3/1994 | Krayer et al. | 235/375 |
| 5,311,790 A | * | 5/1994 | Yanagisawa | 74/490.09 |
| 5,612,603 A | * | 3/1997 | Kim | 318/568.11 |
| 5,934,141 A | * | 8/1999 | Costa | 74/89.17 |
| 6,010,441 A | * | 1/2000 | Angren | 483/1 |
| 6,120,230 A | * | 9/2000 | Brown | 414/273 |
| 6,223,413 B1 | | 5/2001 | Crocker et al. | 29/524.1 |
| 6,254,328 B1 | * | 7/2001 | Wytman | 414/217 |
| 6,264,419 B1 | * | 7/2001 | Schinzel | 414/751.1 |
| 6,654,122 B1 | * | 11/2003 | Hanson et al. | 356/614 |

FOREIGN PATENT DOCUMENTS

| | | |
|---|---|---|
| CH | 690 962 A | 3/2001 |
| DE | 3736419 | 5/1989 |
| DE | 4028059 | 3/1992 |
| DE | 200 04 202 | 7/2000 |
| WO | 98/05753 | 2/1998 |

OTHER PUBLICATIONS

European Search Report dated Feb. 26, 2003.

* cited by examiner

*Primary Examiner*—Charles A. Fox
(74) *Attorney, Agent, or Firm*—Baker & Hostetler LLP

(57) ABSTRACT

The invention pertains to an object storage device with at least two storage spaces for stackers as well as a horizontally tiltable transport platform whose height can be displaced by a hoisting unit. The hoisting unit is arranged at a base point, which can be moved horizontally over an X-Y track system, which has the advantage that, in principle, any number of stackers can be arranged in two parallel rows next to each other. It is preferred that the hoisting unit be suspended from the X-Y track system with the free end hanging down.

11 Claims, 4 Drawing Sheets

OBJECT STORAGE DEVICE AND CLIMATE-CONTROLLED CABINET

FIELD OF THE INVENTION

The invention pertains to an object storage device with at least two storage spaces for cassettes as well as a transport unit for an object which presents a hoisting unit and a horizontally tiltable transport platform. The invention, furthermore, pertains to a climate-controlled cabinet with this object storage device.

BACKGROUND OF THE INVENTION

An object storage device and a climate-controlled cabinet of this type are known from WO 9 8/05753. Typically they are used in the laboratory, particularly in the fields known as the life sciences and materials science. In principle, a large variety of objects can be accommodated in such an object storage device. Standardized objects in this connection are, in particular, microtiter plate (MTP), which are deposited one on top of another in stationary or transportable cassettes (stackers) with a predetermined number of storage surfaces. In an object storage device, several storage spaces for these cassettes are arranged next to each other According to WO 98/05753 the cassette storage spaces are arranged in the form of a carousel on a rotating disk. In order to deposit an object in a storage slot or to remove it from a storage slot, a stationary hoisting unit with a horizontally tiltable transport platform is used. During the process, the given cassette is rotated with the rotating disk to the hoisting unit, the transport platform is displaced to the height of the storage slot and tilted by means of a toggle-lever mechanism in the direction of the storage slot. Using the toggle-lever mechanism, a linear movement of the transport platform toward or away from the object is then performed in order to either receive or deposit the object.

As a result of the system, the ratio of the number of cassette storage spaces to the required surface area worsens as the number of cassette storage spaces increases. In addition, the drive devices for the hoisting unit and the tilting mechanism are arranged in the work space which can be disadvantageous with regard to the cleaning of the work space and its disinfection.

SUMMARY OF THE INVENTION

The invention is based on the problem of indicating an object storage device and a climate-controlled cabinet of the type initially mentioned, which can be fitted with a large number of cassette storage spaces while taking up as little space as possible.

This problem is solved with an object storage device as a result of the fact that the storage spaces are arranged next to each other in at least one row along a passage, and the hoisting unit is arranged at a base point which can be moved horizontally over an X-Y track system in the passage.

The invention has the advantage that a large number of storage spaces can be prepared with a good ratio of storage space surface area to total surface area and that a high degree of automation and access is nonetheless ensured.

The degree of coverage for a given footprint is particularly high because two parallel rows of storage spaces are arranged on both sides of the passage.

In preferred variant of the invention, the X-Y track system is arranged above the storage spaces and the hoisting unit is suspended from the X-Y track system with a free end hanging down.

In this manner, the entire floor surface of the object storage device is kept clear, so that it can be optimally cleaned and disinfected and thus the risk of contamination is prevented.

It is particularly advantageous for the hoisting unit to present a vertical track and a vertical control gear for the transport platform. As a result, simple means can be used to achieve a sufficient rigidity of the hoisting unit even with a large effective length or large vertical distance.

The design is particularly simple because the X-Y track system presents at least a horizontal control gear and a torque transfer device, which function in a self-supporting manner. The space requirements for the X-Y track system become particularly small as a result, and the surfaces to be cleaned can be kept small.

An additional advantageous embodiment of the invention is that the X-Y track system has first and second longitudinal track subassemblies, which together have a longitudinal control gear as well as first and second torque transfer devices, that a transverse track subassembly is arranged in such a manner that it can be displaced on the first and second longitudinal track subassembly, transversely with respect to the latter, where said transverse track subassembly has a transverse control gear and a third torque transfer device, that the longitudinal control gear is in active connection with the transverse track subassembly, in that the control gear is in active connection with the base point of the hoisting unit, that the first torque transfer device acts on the transverse control gear, and that the second torque transfer device acts on the vertical control gear via the third torque transfer device. This design has the advantage that the transport platform can be indirectly controlled with two control gears, wherein the drive and control devices can be arranged outside the work space, in a location which is not critical with regard to the risk of contamination.

In principle, the X-Y track system can be formed with slide tracks in connection with a drawing means. However, the structure can be manufactured in a particularly simple and cost-effective manner by constructing each of the longitudinal, transverse and vertical control gear as worm gears with longitudinal, transverse or vertical threaded spindles. As a result, the control paths can be implemented with high precision. In addition, the threaded spindles can be constructed with sufficient stability and flexural strength that they also take on the function of a guide and support track.

It is very advantageous for the first, second and third horizontal torque transfer devices to be designed as first, second and third torque shafts, respectively. In the context of the track system, they can also take on guide and support functions, particularly in connection with the threaded spindles. Particularly in the case of the transverse track subassembly it is possible, in this manner, to omit the use of additional support and guide tracks.

The entire X-Y track system can be carried out so that it is practically self-supporting due to the fact that the first longitudinal track subassembly comprises the first torque shaft, and the second longitudinal track subassembly consists of the first threaded spindle and the second torque shaft, and the transverse track subassembly consists of the second threaded spindle and the third torque shaft.

With regard to decreasing the risk of contamination it is furthermore highly advantageous that drive devices be arranged at the end of the first and second torque shaft, as well as of the longitudinal threaded spindle, and that the drive devices be arranged outside of an internal housing space, where the first and second torque shafts are led through the wall of an internal housing space.

The X-Y track system with the hoisting unit and the transport platform can be completely removed from the internal space for cleaning or replacement quickly and simply since it is arranged on a bottom frame with four corner braces, and it is attached in a removable manner to the upper end areas of the corner braces.

In this context, it is advantageous, for the purpose of preventing heat/cold bridges, that the ends of the first and second torque shaft and of the threaded spindle, which are led out of the internal space, are provided with a temperature-insulating intermediate part in the outlet area.

A preferred variant of the invention consists in that, on the transport platform, an entraining element is rotatably attached and a stop is arranged in a fixed position at a predetermined height, in that the stop can be brought into active connection with the entraining element by changing the height of the transport platform so that, as a result of the horizontal displacement of the transport platform, the entraining element engages with the stop in this position, and the transport platform is horizontally tilted.

A particularly precise angular control is achieved by indirect means as a result of the fact that the entraining element is designed as a toothed wheel and the stop as a toothed rack, so that the toothed wheel can be made to mesh with the toothed rack by a displacement in the height of the transport platform, and as a result of a horizontal displacement of the transport platform, it travels out in this position against the toothed rack.

The positioning precision, moreover, is further improved by the fact that the transport platform is arranged in a manner so it can be tilted on a slide part which is rotatably arranged on the vertical track and by the fact that between the transport platform and the slide part, position adjusting devices are arranged in predetermined tilt angle positions.

The access paths and the access times are particularly short, as a result of the arrangement of the toothed rack along the entire length and/or transverse displacement path of the transport platform.

However, in principle, it is sufficient for the length of the toothed rack to correspond, at most, to the circumference of the toothed wheel.

The exact orientation of an object on the transport platform is guaranteed by the fact that in the receiving area of the transport platform a lateral stop is arranged for an object to be received and by the fact that, in a position opposite the lateral stop, a slide is arranged, which is under pretension due to a spring in the direction toward the stop, for pressing the received object against the stop.

In order further to decrease the risk of contamination, it is advantageous to use contact-free position sensors and/or angle indicators, whose receiving space is arranged outside of the internal wall space. It is preferred to use inductive position sensors and/or inductive angle indicators. It is particularly advantageous for the inductive position sensors and/or inductive angle indicators to be adapted to a transfer section where aluminum is located, so that the internal wall space can be made from aluminum sheet metal. The position sensors and angle indicators are preferably used to determine a zero reference point for the control of the movement of the torque shafts and of the threaded spindles.

The object storage device is used particularly advantageously in a climate-controlled cabinet. It is equally well suited for incubators, particularly gas-operated incubators, such as for freezing and cooling apparatuses.

BRIEF DESCRIPTION OF THE DRAWING

The invention is further described below with reference to an embodiment example represented in the drawing. Shown schematically are.

DETAILED DESCRIPTION OF THE PREFERRED EMBODIMENT

Figure 1:
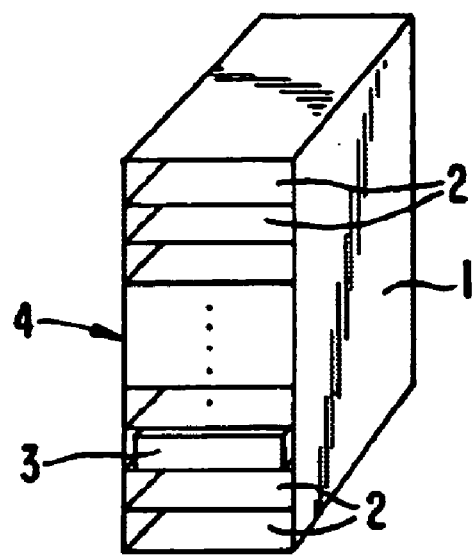
FIG. 1, a perspective view of a cassette for receiving objects.

FIG. 1 depicts a cassette 1 with a multitude of shelf-like storage slots 2, which are arranged one on top of another, each for an object 3, for example, a microtiter plate. The storage slots 2 can be accessed from a front side 4 in such a way that an object 3 can be deposited in a storage slot 2 or removed from a storage slot 2.

Figure 2:
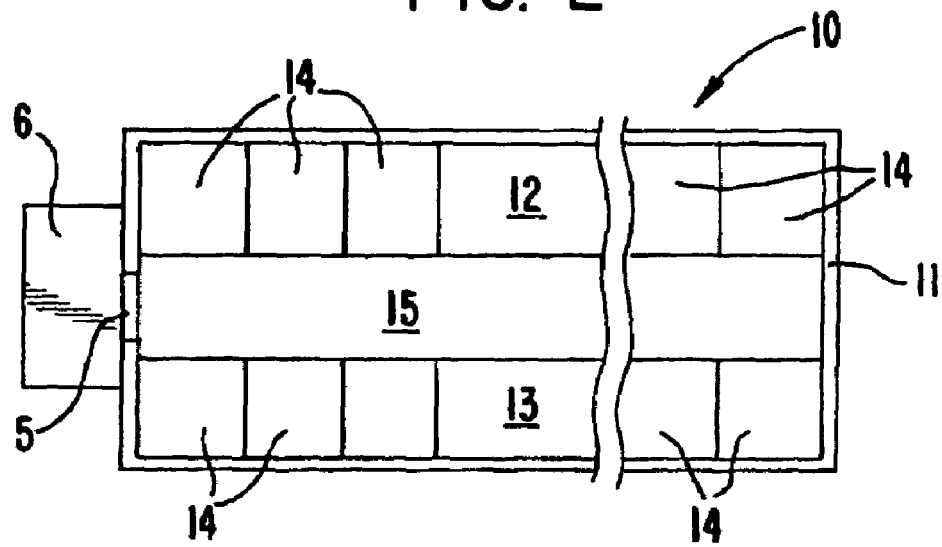
FIG. 2, a plan of an object storage device.
Figure 3:
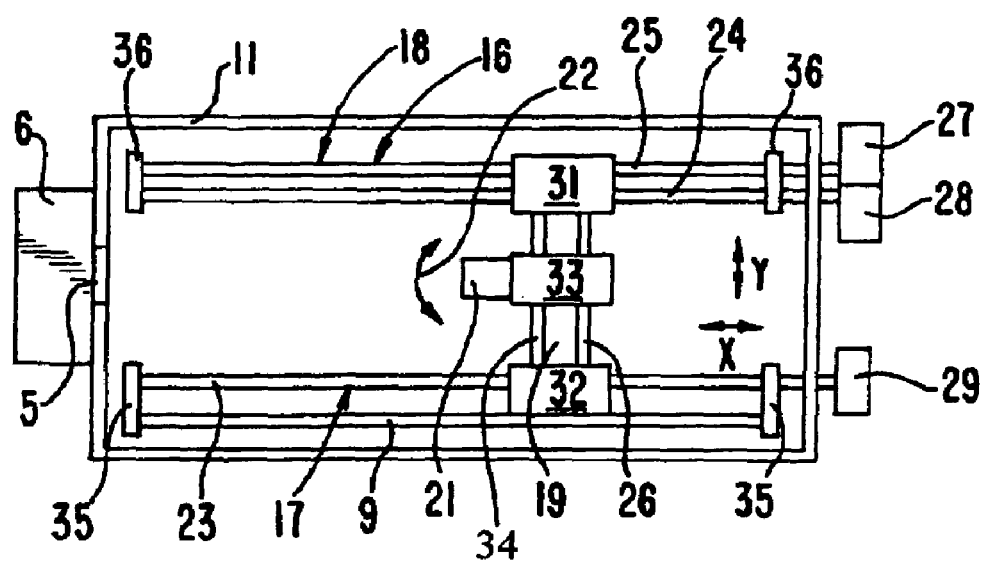
FIG. 3, a top view of an X-Y track system in an object storage device according to FIG. 2.

According to FIG. 2, the plan of an object storage device is represented using the example of a climatic chamber 10, which is surrounded by an internal wall 11. In the interior of the climatic chamber 10, two parallel rows 12, 13 of storage spaces 14 for cassettes 1 (FIG. 1) are arranged along a passage 15. Each storage space 14 can receive a cassette 1. The accessible front sides 4 of the cassettes 1 are all turned toward the passage 15, so that all the storage slots 2 are accessible from the passage 15 to a transport platform 21 (FIG. 3). At the end of the passage 15, a closable opening 5 leading to a transfer station 6 is located in the internal wall 11 for the purpose of moving individual objects by means of the transport platform 21 into the climatic chamber 10 or out of the climatic chamber 10.

FIG. 3 shows, from above, a horizontally running X-Y track system 16, which is arranged in the interior of the climatic chamber 10. The X-Y track system 16 comprises first and second longitudinal track subassemblies 17, 18 as well as a transverse track subassembly 19 which runs orthogonally thereto, and which is placed so it can be longitudinally displaced on the two longitudinal track subassemblies 17, 18.

Figure 4:
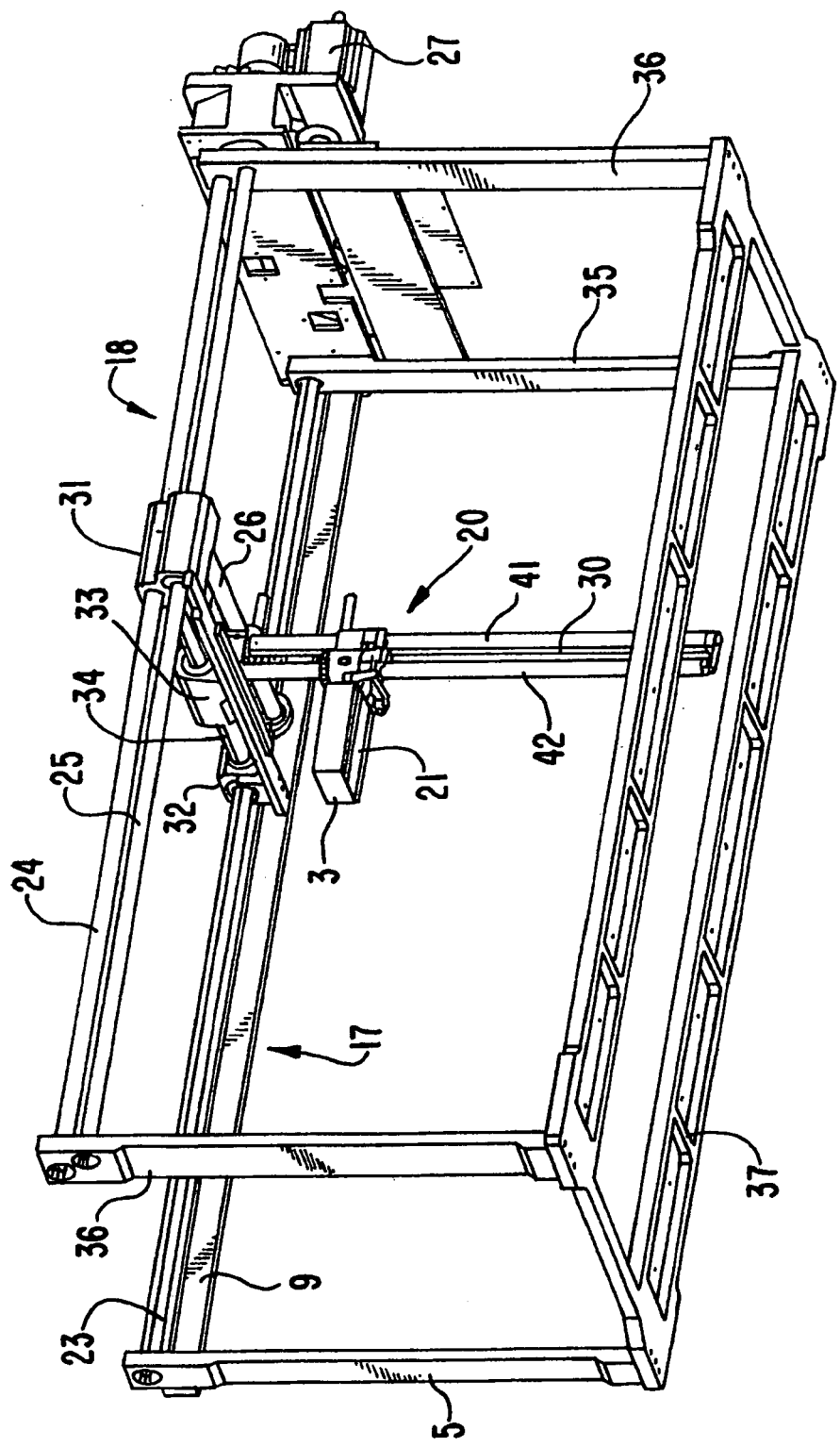
FIG. 4, a perspective view of the X-Y track system of FIG. 3 from below.

The X-Y track system 16 rests on four corner posts 35, 36, which are applied on a floor frame 37 (FIG. 4). The cassette storage spaces 14 are also on the floor frame 37. The X-Y track system 16, including a vertical track subassembly 30, can be removed for cleaning and maintenance work from the corner posts 35, 36 and from the climatic chamber 10.

FIG. 4 shows the X-Y track system 16 with the corner posts 35, 36 and the floor frame 37. To keep the representation simple, details of the climatic chamber 10 are not represented. Furthermore, a perspective view from below is chosen in order to depict the vertical track subassembly 30 which is suspended on the transverse track subassembly 19, including the hoisting unit 20 for the transport platform 21.

According to FIGS. 3 and 4, the vertical track subassembly 30 is arranged on the transverse track subassembly 19 in such a manner that it can be displaced transversely, with the hoisting unit 20, by means of which a transport platform 21, which can be tilted horizontally according to the arrow 22 can be displaced in its height (vertically with respect to the plane of the drawing) to convey an individual object 3.

The first longitudinal track subassembly 17 comprises a torque transfer device in the form of a first torque shaft 23 and, furthermore, in the present embodiment example, of a slide track 9. The second longitudinal track subassembly 18 comprises a longitudinal control gear in the form of a longitudinal threaded spindle 24 as well as a second torque transfer device in the form of a second torque shaft 25. The longitudinal track subassemblies 17, 18 completely bear the weight of the transverse track subassembly 19 including the vertical subassembly 30 with hoisting unit 20 and transport platform 21 and its load. The slide track 9 can be particularly advantageous if the length of the first longitudinal track subassembly 17 is long. It runs adjacent to the first torque shaft 23 and it bears a portion of the load of the transverse track subassembly 19.

The transverse track subassembly 19 consists, in a self-supporting manner, of a transverse control gear in the form of a transverse threaded spindle 26 as well as a third torque transfer device in the form of a third torque shaft 34. It completely bears the load of the vertical track subassembly 30.

Outside of the internal wall 11 of the climatic chamber 10, a longitudinal drive device 27, a transverse drive device 28 and a vertical drive device 29, each in the form of a stepper motor, are arranged, by means of which the transverse track subassembly 19 and the base point of the vertical track subassembly 30 can be moved in the horizontal plane and the transport platform 21 vertically. The three drive devices 27, 28, 29 are mounted in a fixed manner on the climatic chamber 10.

The longitudinal drive device 27 acts on the free end of the longitudinal threaded spindle 24, which acts via a spindle nut (not shown) on a storage carriage 31 of the transverse track subassembly 19. The vertical drive device 29 acts on the first torque shaft 23, which acts via a miter gear (not shown) on an additional storage carriage 32 on the first torque shaft 23. The latter transfers the torque via an additional miter gear (not shown) on an additional storage carriage 33 to a third torque shaft 34 (FIG. 4). The transverse drive device 28 applies the second torque shaft 25, which is in active connection via a miter gear (not shown) on the storage carriage 31 with the transverse threaded spindle 26, which acts on a third storage carriage 33 with spindle nut (not shown) of the vertical track subassembly 30.

The first torque shaft 23 and the slide track 9 are placed in two corner posts 35, and the second torque shaft 25 as well as the longitudinal threaded spindle 24 are placed in two additional corner posts 36. The drive-side bearings are designed as fixed bearings and the bearing to the for any tolerances and temperature-related changes that may occur, and load on the connection of shafts and drive devices is relieved.

Figure 5:
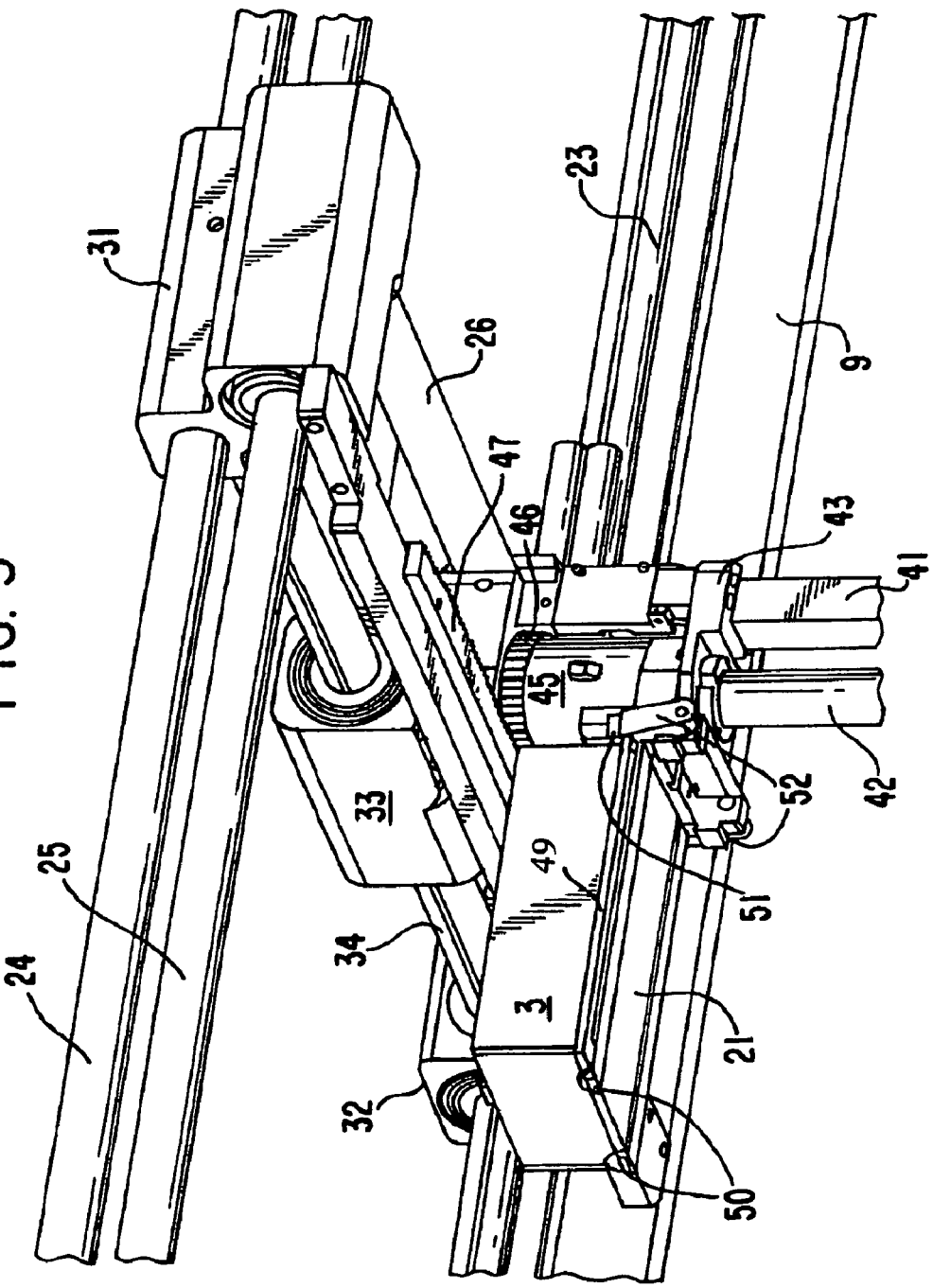
FIG. 5, a perspective view of the hoisting unit of FIGS. 3 and 4 from below in an enlarged representation.

FIG. 5 shows, in an enlarged representation, details of a tilt mechanism, by means of which a horizontal tilting movement of the transport platform 21 can be controlled and executed. The vertical track subassembly 30 consists of a vertical track 41 and a vertical control gear in the form of a vertical threaded spindle 42. The vertical track 41 and the vertical threaded spindle 42 form a hoisting unit 20 for the transport platform 21. The free ends of the vertical track 41 and of the vertical threaded spindle 42 are located freely in space.

A base part 43 is rotatably guided in such a way that it can be displaced on the vertical track 41 and the vertical threaded spindle 42. On the base part 43, a spindle nut (not shown), which is actuated by the vertical threaded spindle 42, acts to vertically displace the transport platform 21.

The base part 43 carries a holder 45, to which the transport platform 21 is rotatably attached. The holder 45 is rotatably attached on the base part 43 about the vertical threaded spindle 42. The holder 45, furthermore, presents a toothed wheel 46 which is concentric with the vertical threaded spindle 42. A rotation of the toothed wheel 46 effects the tilting of the transport platform 21.

Along a partial part of the transverse displacement path of the vertical track 41 or the transport platform 21 along the transverse track subassembly 19, on the transverse track subassembly 19, a toothed rack 47 is arranged which is stationary with respect to the vertical track 41 or the transport platform 21. The toothed rack 47 is located at a predetermined height at the end of the vertical displacement path of the transport platform 21.

As a result of a displacement in the height of the holder 45 or of the transport platform 21, the toothed wheel 46 is made to mesh with the toothed rack 47. When the vertical track 41 with the holder 45 and the transport platform 21 is moved horizontally along the transverse track subassembly 19, the toothed wheel 46 turns against the toothed rack 47, which effects a tilting of the transport platform. The angle of tilt is here a function of the length of the horizontal displacement path of the transport platform 21. This tilting movement is thus controlled and executed indirectly by the cooperation of the transverse drive device 28 and the vertical drive device 29.

The passage 15 is dimensioned such that the vertical track subassembly 30, including a received object 3, can be moved along all the cassettes 1 and all the storage slots 2 in the two rows 12, 13.

Figure 6:
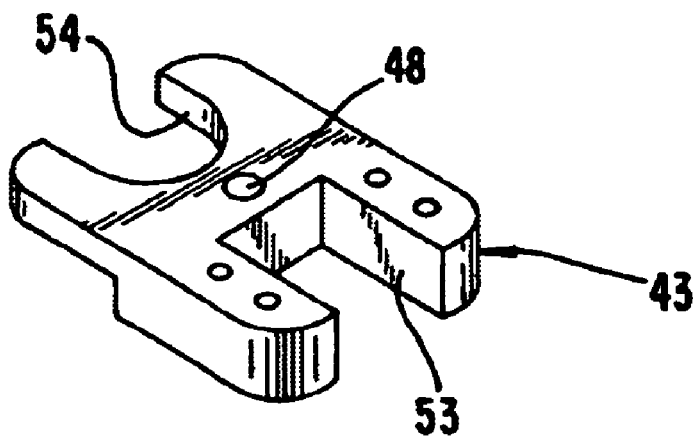
FIG. 6, a detail of the hoisting unit according to FIG. 5.

In order to take objects 3 from the transfer station 6 with a defined orientation or to place them in such an orientation, and to be able to properly manipulate the storage slots 2, in an object storage device according to FIG. 2 with two rows 12 13 at least three tilt angle positions of the transport platform 21 must be precisely maintained, where the positions are displaced by 90°. For this purpose, according to FIG. 6, a notched positioning system in the form of a ball-pressure part 48 is arranged on the base part 43, which works in cooperation with three recesses on the bottom side of the holder 45. As soon as the holder 45 reaches one of the three positions which are displaced by 90°, the ball pressure part 48 engages. On the base part 43 a first recess 53 is present, by means of which it is guided over the vertical track 41. A second recess 54 is used for the rotational mounting of the holder 45.

At the free end of a receiving area 49 of the transport platform 21, stops 50 for an object 3 to be received are arranged, which guarantee a precise positioning of the object 3 on the receiving area 49. Opposite the stops 50, a slide 51, which is under pretension due to a spring, is located, which can be tilted out via the lever arms 52 in the direction toward the stops 50. The slide 51 orients the object 3 toward the stop 50 and it holds the object 3 fixed as a result of the compression of the spring.

The slide 51 is furthermore controlled by a stop on the cassette side and a stop (not shown) in the area of the transfer station 6 in such a way that it is displaced back against the spring force and releases the object 3.

The invention claimed is:

1. An object storage device comprising: at least two storage spaces for object cassettes, wherein the storage spaces are arranged next to each other in at least one row along a passage;

a horizontally tiltable transport platform;

a hoisting unit for displacing the height of the platform, wherein the hoisting unit is arranged at a base point, wherein the base point is horizontally displaced over an X-Y track system, wherein the X-Y track system comprises first and second longitudinal track subassemblies, wherein the first and second longitudinal track subassemblies includes a longitudinal control gear, and first and second torque transfer devices; and a displaceable transverse track subassembly transversely placed on the first and second longitudinal track subassemblies, and including a transverse control gear and a third torque transfer device, wherein the longitudinal control gear is mechanically coupled with the transverse track subassembly, wherein the transverse control gear is mechanically coupled with the base point, wherein first torque transfer device acts on the transverse control gear and the second torque transfer device acts on the transverse control gear via the third torque transfer device.

2. The object storage device according to claim 1, further comprising two parallel rows of storage spaces arranged on either side of the passage.

3. The object storage device according to claim 1, wherein the hoisting unit presents a vertical track and a vertical control gear for the transport platform.

4. The object storage device according to 3, wherein the longitudinal, transverse and vertical control gears comprise worm gears with a longitudinal, transverse or vertical threaded spindle.

5. The object storage device according to claim 4, wherein the X-Y track system presents at least one horizontal control gear and a torque transfer device, which, in a self-supporting manner, function as a track.

6. The object storage device according to claim 4, wherein the first, second and third torque transfer devices comprise first, second and third torque shafts respectively.

7. The object storage device according to claim 6, wherein the first longitudinal track subassembly comprises the first torque shaft, and the second longitudinal track subassembly comprises the longitudinal threaded spindle and the second torque shaft, and in that the transverse track subassembly comprises the transverse threaded spindle and the third torque shaft.

8. The object storage device according to claim 6, further comprising an internal space housing, in that the first and second torque shafts and the longitudinal threaded spindle, to the ends of which a drive device acts, are led out of the internal housing space, and in that the drive devices are arranged outside of the internal housing space.

9. The object storage device according to claim 8, wherein the ends of the first and second horizontal torque shaft and the longitudinal threaded spindle, which are led out of the internal housing space, are provided, with a temperature insulating intermediate part.

10. The object storage device according to claim 3, further comprising a climatic chamber having a cover area, such that the first and second torque shafts and the longitudinal threaded spindle, together with a third torque shaft and the transverse threaded spindle are arranged in the cover area, such that the vertical track and the vertical threaded spindle are suspended from the third torque shaft and the transverse threaded spindle.

11. The object storage device according to claim 1, further comprising an entraining element rotatably attached on the transport platform and a stop is arranged in a stationary position at a predetermined height, in that the stop can be brought into active connection with the entraining element by displacing the height of the transport platform, so that, the entraining element turns against the stop, and the transport platform is tilted.

* * * * *